(12) United States Patent
Lu et al.

(10) Patent No.: US 11,179,425 B2
(45) Date of Patent: Nov. 23, 2021

(54) METHOD OF ACTIVATING TUMOR-INFILTRATING LYMPHOCYTES (TILS)

(71) Applicant: Microbio Co. Ltd., Taipei (TW)

(72) Inventors: Kung-Ming Lu, Taipei (TW); Min-Liang Kuo, Taipei (TW); Ai-Jen Yang, Taipei (TW)

(73) Assignee: MICROBIO CO., LTD., Taipei (TW)

( * ) Notice: Subject to any disclaimer, the term of this patent is extended or adjusted under 35 U.S.C. 154(b) by 192 days.

(21) Appl. No.: 16/243,325

(22) Filed: Jan. 9, 2019

(65) Prior Publication Data

US 2019/0209623 A1    Jul. 11, 2019

Related U.S. Application Data

(60) Provisional application No. 62/615,300, filed on Jan. 9, 2018.

(51) Int. Cl.
| | | |
|---|---|---|
| *A61K 35/74* | (2015.01) | |
| *A61P 35/00* | (2006.01) | |
| *A61K 36/06* | (2006.01) | |
| *A61K 9/00*  | (2006.01) | |

(52) U.S. Cl.
CPC ............ *A61K 35/74* (2013.01); *A61K 9/0019* (2013.01); *A61K 36/06* (2013.01); *A61P 35/00* (2018.01)

(58) Field of Classification Search
CPC ........ A61K 35/744; A61K 35/06; A61P 35/00
See application file for complete search history.

(56) References Cited

U.S. PATENT DOCUMENTS

2003/0008023 A1* 1/2003 Lu .............................. A61P 9/10
424/757

FOREIGN PATENT DOCUMENTS

| CN | 1375314 A | 10/2002 |
|---|---|---|
| CN | 1720954 A | 1/2006 |
| CN | 104415298 A | 3/2015 |
| TW | 252759 B | 4/2006 |
| WO | WO 2017/167213 A1 | 10/2017 |

* cited by examiner

*Primary Examiner* — Daniel C Gamett
(74) *Attorney, Agent, or Firm* — McDermott Will & Emery LLP (57) ABSTRACT

The present invention relates to a method for activating tumor-infiltrating lymphocytes (TILs) in a subject in need, particularly by administering to the subject a fermented composition generated via fermentation of symbiotic microbiota in a medium.

18 Claims, 8 Drawing Sheets

METHOD OF ACTIVATING TUMOR-INFILTRATING LYMPHOCYTES (TILS)

RELATED APPLICATION

This application claims the benefit of U.S. provisional application No. 62/615,300, filed Jan. 9, 2018 under 35 U.S.C. § 119, the entire content of which is herein incorporated by reference.

TECHNOLOGY FIELD

The present invention relates to a method for activating tumor-infiltrating lymphocytes (TILs) in a subject in need, particularly by administering to the subject a fermented composition generated via fermentation of symbiotic microbiota in a medium.

BACKGROUND OF THE INVENTION

Tumor infiltrating lymphocytes (TILs) are populations of immune cells that are actively recruited to the tumor site to initiate an immune response against tumor growth and metastasis. TILs have been shown to directly attack tumor tissues and correlate with response to checkpoint blockage and favorable clinical outcomes. However, activation of TILs is not always possible or sufficient in all of the patients. Further, it has been reported that cancer cells may cause microenvironment changing and suppression of anti-tumor immunity, leading to insensitivity or tolerant to cancer drugs/therapy. There is a need for activation of TILs or enhancement of sensitivity to immunotherapy of a subject particularly against cancer.

BRIEF SUMMARY OF THE INVENTION

The present invention is based on the unexpected finding that a fermentation product by symbiotic microbiota as described herein is effective in activating tumor infiltrating cells (TILs) in tumor animal models, particularly promoting migration of TILs into tumor and increasing the amount of TILs inside tumor, thus transforming cold tumor to hot tumor and changing immunosuppressive tumor microenvironment to immuno-responsive tumor microenvironment, leading to enhanced anti-cancer therapeutic effects, especially in combination with an immune checkpoint modulator. It is also found that intratumoral administration of a fermentation product by symbiotic microbiota as described herein provides improved therapeutic effects where the dosing amount is reduced, the dosing course is shorten, and even tumors in distant sites thought to be unresponsive can also be successfully treated.

Therefore, one aspect of the present invention is to provide a method for activating TILs in a subject in need thereof, comprising administering to the subject a fermented composition generated via fermentation of symbiotic microbiota in a medium, wherein the symbiotic microbiota comprises (i) at least two or more lactic acid bacteria strains, or (ii) at least two or more yeast strains, or (iii) at least one or more lactic acid bacteria strains and at least one or more yeast strains, in an amount effective in increasing production or activity of TILs in the subject.

In some embodiments, the medium for fermentation comprises a carbon source, a nitrogen source and trace elements In some embodiments, the medium fermented composition comprises multiple metabolites that are generated via the fermentation.

In some embodiments, the fermented composition is prepared by a process comprising
(i) growing the symbiotic microbiota in the medium under conditions allowing for fermentation to generate multiple metabolites; and
(ii) collecting the fermented composition obtained from step (i).

In some embodiments, the preparation process further comprises sterilizing, filtering and/or concentrating the fermented composition obtained from step (ii).

In some embodiments, the fermented composition is effective in (i) changing tumor microenvironment to avoid suppression of anti-tumor immunity, and/or (ii) improving effects of chemotherapy and/or cancer therapy, and/or (iii) transforming cold tumor into hot tumor, and/or (iv) increasing response rate, and/or (v) reducing tumor size, and/or (vi) improving survival rates, in the subject.

In some embodiments, the subject is afflicted with a neoplastic disease.

In some embodiments, the subject is afflicted with cancer.

In some embodiments, the subject is afflicted with bacteria infected tumor.

In some embodiments, the cancer selected from the group consisting of colon cancer, lung cancer, breast cancer, pancreatic cancer, skin cancer, brain cancer, ovarian cancer, kidney cancer, stomach cancer, head and neck cancer, esophageal cancer, bladder cancer, rectal cancer, bone cancer, uterine cancer, prostate cancer, and hematological malignancy.

In some embodiments, the subject has undergone, is undergoing or is planning to undergo an immune therapy against a neoplastic disease e.g. using an immune checkpoint modulator.

In some embodiments, the method comprises selecting a subject in need of activation of TILs prior to the administration of the fermentation composition.

In some embodiments, the subject has been determined to have a relatively lower level of TILs as compared to a reference level.

In some embodiments, the TILs include CD4+, CD8+ and/or CD86+dendritic cells.

In some embodiments, the fermented composition is administered via oral administration or injection administration. In other embodiments, the fermented composition is administered via intratumoral administration.

Also within the scope of the present invention are fermented compositions generated via fermentation of symbiotic microbiota in a medium as described herein for use in activating TILs in a subject in need thereof. The present invention also features use of a fermented composition generated via fermentation of symbiotic microbiota in a medium as described herein for manufacturing a medicament for activation of TILs in a subject in need. The present invention further provides a kit or combination comprising a fermented composition generated via fermentation of symbiotic microbiota in a medium as described herein, optionally in combination with an immune checkpoint modulator, for use in activating TILs in a subject in need thereof. In some embodiments, the kit or combination is useful in (i) changing tumor microenvironment to avoid suppression of anti-tumor immunity, and/or (ii) improving effects of chemotherapy and/or cancer therapy, and/or (iii) transforming cold tumor into hot tumor, and/or (iv) increasing response rate, and/or (v) reducing tumor size, and/or (vi)

improving survival rates, in the subject. Preferably, the kit or combination provides a synergistic effect.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings

DETAILED DESCRIPTION OF THE INVENTION

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "comprise" or "comprising" is generally used in the sense of include/including which means permitting the presence of one or more features, ingredients or components. The term "comprise" or "comprising" encompasses the term "consists" or "consisting of."

As used herein, the term "neoplastic disease" refers to an abnormal mass of tissue as a result of neoplasia i.e. the abnormal proliferation of cells. The growth of these cells exceeds that of normal tissues around it. It usually, but not always, produces a lump or tumor. A neoplastic disease may be benign, pre-malignant or malignant. As used herein, cancer refers to a general term for diseases caused by any type of malignant tumor, including any stage (stage I cancer, stage II cancer, stage III cancer, stage IV cancer), grade (grade I cancer, grade II cancer, grade III cancer), invasiveness, aggressiveness or malignancy of an affected tissue or cell aggregation. Unless defined otherwise, the terms "neoplastic disease," "tumor" and "cancer" are not limited to any tissues or cell type and include primary, secondary or metastatic lesions.

As used herein, the term "tumor microenvironment (TME)" refers to the environment in which a tumor exists, including tumor cells themselves, the surrounding stromal cells and non-cellular components, such as cytokines, chemokines, collagen, elastin, and growth factors. The stromal cells include fibroblasts, epithelial cells, vascular cells, resident and/or recruited inflammatory and immune cells (e.g., macrophages, dendritic cells, granulocytes, lymphocytes, etc.) that modulate tumor cell growth or survival. In early or middle stage of tumor, some tumor cells acquire mutations that allow them to resist immune destruction, but their proliferation and spread are still restricted by immune responses. Major anti-tumor components include natural killer (NK) cells, cytolytic T lymphocytes (CTLs), $CD4^+$ helper T cells, M1 macrophages and two major cytokines: interleukin-12 (IL-12) and interferon-$\gamma$ (IFN-$\gamma$). However, advanced tumor cells often changes the tumor microenvironment, shifting from immuno-responsive to immunosuppressive, allowing tumor cells to evade from host immunosurveillance and supporting tumor growth, progression and spread. Specifically, in the immunosuppressive tumor microenvironment, although some immune cells, such as cytotoxic CTLs or helper T cells, may still exist, their function is largely inhibited; IL-12 production is also greatly suppressed; and cell subsets associated with immune suppression such as regulatory T cells (Tregs), myeloid derived suppressor cells (MDSC) and M2 macrophages are recruited to the tumor site, leading to inhibition of immune activity; on the other hand, tumor cells produce cytokines, such as tumor necrotic factor-α (TNFα) and cyclooxygenase-2 (Cox-2), which promote chronic inflammation and vascular endothelial growth factor (VEGF) that promotes angiogenesis, both leading to significant tumor growth.

As used herein, the term "tumor infiltrating lymphocytes (TILs)" are populations of immune cells that are associated with tumor tissue. More particularly, TILs are lymphocytes of a subject afflicted with a cancer that have left the blood stream and have associated with a tumor. Therefore, TILs may have tumor specificity and activating TILs may allow for more direct control of the elimination of tumor cells. The main types of TILs include T cells, B cells and natural killer (NK) cells. Cytotoxicity T lymphocytes (CTLs), particularly $CD8^+$ cells, can directly attack and kill tumor cells. T helper lymphocytes (Th), particularly $CD4^+$ cells, are capable of secreting various cytokines that can activate CTLs. TILs also include myeloid cells such as dendritic cells, particularly $CD86^+$ dendritic cells. The presence of TILs, particularly $CD8^+$ cells, in tumors is known to be positively associated with good response to immunotherapy particularly using immune checkpoint modulator(s), advantageous in changing the tumor microenvironment from immunosuppressive to immuno-stimulatory, transforming cold tumor into hot tumor, and leads to better clinic outcomes. Intratumoral TILs may be defined as lymphocytes inside tumor nests having cell-to-cell contact with no intervening stroma and directly interacting with tumor cells, while stromal TILs may be defined as lymphocytes located dispersed in the stroma between the tumor cells and do not directly contact tumor cells. TILs can be assessed, identified, accounted and/or phenotyped by immunohistochemistry analysis and flow cytometric analysis with antibody labeling. The International TILs Working Group has proposed a method to assay the presence and quantity of TILs by measuring the area occupied by mononuclear cells over the stromal area on hematoxylin and eosin (H-E) stained sections in breast cancer which is also applicable in colorectal cancer. See Iseki et al., PLoS One. 2018 Apr. 26; 13(4):e0192744. In addition, quantification of TILs can be carried out using droplet digital PCT (ddPCR) technology. See Robins et al., Sci Transl Med. 2013 Dec. 4; 5(214):214ra169.

As used herein, the term "activating TILs" or "activation of TILs" may include increasing TILs' activity/number/density in a tumor tissue sample from a cancer subject compared to a reference or control level, for example, by at least 5%, 10%, 15%, 20%, 25%, 30%, 35%, 40%, 45%, 50%, 55%, 60%, 65%, 70%, 75%, 80%, 85%, 90%, 95% or 98%. A reference or control level can refer to the level measured in an individual (or an average level in a population of individuals) prior to or without treatment as described herein.

As used herein, the term "hot tumor" or "inflamed tumor" refers to a tumor wherein there is a considerable presence of anti-tumor immune cells especially TILs and thus are typically immuno-stimulatory.

As used herein, the term "cold tumor" or "non-inflamed tumor" refers to a tumor wherein there is no or minimal presence of anti-tumor immune cells especially TILs or instead containing cell subsets associated with immune suppression including regulatory T cells (Treg), myeloid-derived suppressor cells (MDSCs) and M2 macrophages. Specifically, cold tumor may be characterized by a low number or even absence of infiltration of anti-tumor immune cells that such cells may be present but remain stuck in the surrounding stroma, thus unable to colonize the tumor microenvironment to provide their antitumor functions.

As described herein, TILs have been known to play an important role of directly attacking tumor cells in a variety of types of cancer and a number of studies have demonstrated that the presence of TILs are highly correlated with therapeutic effects and increased survival in cancer patients. It is unexpected found that a fermented composition generated via fermentation of symbiotic microbiota in a medium as described herein successfully activated TILs in an animal cancer model. In some instances, a fermented composition as described herein is demonstrated to exhibit synergistic effects in treating cancer with an immune modulator. The results of this study show that a fermented composition as described herein may facilitate changes from suppression to enhancement of anti-tumor immunity, transformation of cold tumor transforms into hot tumor, increase of the response rate of anti-cancer immune therapy e.g. using an immune checkpoint modulator increases, reduction of tumor size and improvement of survival rates. Further, in some instances, intratumoral administration of a fermentation product by symbiotic microbiota as described herein is demonstrated to provide improved therapeutic effects where the dosing amount is reduced, the dosing course is shorten, and even tumors in distant sites thought to be unresponsive can also be successfully treated.

Therefore, one aspect of the present invention relates to a method for activating TILs in a subject in need thereof, comprising administering to the subject a fermented composition generated via fermentation of symbiotic microbiota in a medium as described herein.

Fermentation is a metabolic process, in which microorganisms convert carbohydrates to acids (e.g., organic acids such as lactic acids), alcohols (e.g., ethanol) and/or other metabolites under anaerobic conditions. The fermented composition for use in activation of TILs as described herein is a fermentation product which is generated via fermentation of symbiotic microbiota in a medium. Suitable microorganisms include, but are not limited to, yeast and lactic acid bacteria. Specifically, the symbiotic microbiota as used herein to generate the fermented composition comprises (i) at least two or more lactic acid bacteria strains, or (ii) at least two or more yeast strains, or (iii) at least one or more lactic acid bacteria strains and at least one or more yeast strains. In addition, the fermented composition comprises multiple metabolites generated from the fermentation. In some embodiments, the fermented composition may comprise a combination (e.g., two or more) of lactic acid, acetic acid, and 3-aminoisobutyric acid. In one example, the fermented composition comprise lactic acid at 5-20% by weight (e.g., 5-10%, 10-20%, 5-15% or 15-20% by weight), acetic acid at less than 5% by weight (e.g. 1-5%, 0.5-5%, 1-3%, 0.5-3%, or 3-5% by weight), and 3-aminoisobutyric acid at less than 5% by weight (e.g. 1-5%, 0.5-5%, 1-3%, 0.5-3%, or 3-5% by weight).

Examples of lactic acid bacteria may include bacteria belonging to the genus *Lactobacillus* such as *Lactobacillus acidophilus, Lactobacillus delbrueckii bulgaricus, Lactobacillus lactis lactis, Lactobacillus kefir, Lactobacillus kefiranofaciens*; bacteria belonging to the genus *Lactococcus* such as *Lactococcus lactis, Lactococcus plantarum* and *Lactococcus raffinolactis*; and bacteria belonging to the genus *Bifidobacterium* such as *Bifidobacterium breve, Bifidobacterium longum, Bifidobacterium lactis*. Example of yeast may include yeast belonging to the genus of *Saccharomyces* and *Candida*.

In certain embodiments, the fermentation is carried out using a heterogeneous culture of lactic acid bacteria e.g. *Lactobacillus*, for example, a culture of two (2) or more e.g. 2, 5, 10, 15, 20, 25 or 30 or more strains of *Lactobacillus*. The strains of *Lactobacillus* that can be used in the fermentation include, but are not limited to, *Lactobacillus acidophilus* CCRC (Bioresource Collection and Research Center at Food Industry Research and Development, Taiwan) 10695, 14026, 14064, 14065 and/or 14079, *Lactobacillus delbrueckii bulgaricus* CCRC 10696, 14007, 14009, 14010, 14069, 14071, 14098 and/or 16054, *Lactobacillus lactis lactis* CCRC 10791, 12267, 12306, 12312, 12315, 12323, 14016, 14015 and/or 14117, *Lactobacillus kefyr* CCRC 14011, and/or *Lactobacillus kefiranofaciens* CCRC 16059. Other lactic acid bacteria e.g. *Lactobacillus* can be used in the fermentation, examples of which include, but are not limited to, *Lactococcus chungangensis* (DSM 22330), *Lactococcus formosensis* (BCRC 80576), *Lactococcus fujiensis* (DSM 27937), *Lactococcus garvieae* (BCRC 17074T; ATCC 43921, 49157), *Lactococcus lactis Beijerinck* (ATCC 49032), *Lactococcus lactis* subsp. *Cremoris* (BCRC 12263, 12264, 12265, 12277, 12278, 12303, 12304, 12586T; ATCC 14365), *Lactococcus lactis* subsp. *Hordniae* (BCRC 80474T, ATCC 29071), *Lactococcus lactis* subsp. *Lactis* (BCRC 11068, 12266, 12312T, 12322, 14016, 14105, 14117, 10791, 12315), *Lactococcus lactis* subsp. *Tructae* (BCRC 80475T), *Lactococcus piscium* (ATCC 700018T; DSM 6634), *Lactococcus plantarum* (ATCC 43199), *Lactococcus raffinolactis* (BCRC 14039T; ACTT43920), *Lactococcus taiwanensis* (BCRC 80460T), and *Lactococcus hircilactis* (DSM 28960). In certain embodiments, the fermentation is carried out using a heterogeneous culture of yeast, e.g. *Saccharomyces*, for example, a culture of two (2) or more e.g. 2, 5, 10, 15, 20, 25 or 30 or more strains of *Saccharomyces*. The yeast strains that can be used in the fermentation include, but are not limited to, *Saccharomyces cerevisiae* CCRC 20577, 20578, 20581, 21494, 21550, 21797, 21805, 22138, 22234, 22337, 22731 and/or 22728, and/or *Candida kefyr* CCRC 21269, 21742 and/or 22057. In certain embodiments, a heterogeneous culture as used herein comprises a mixture of at least one or more lactic acid bacteria strains and at least one or more yeast strains. In certain embodiments, a heterogeneous culture as used herein comprises at least one or more *Lactobacillus* strains, at least one or more *Lactococcus* strains and at least one or more yeast strains.

Culture medium suitable for carrying out fermentation of microorganisms is known and available in this art. A typical medium comprises a carbon source such as dextrose, sucrose, fructose, maltose, starch, lactose, etc., a nitrogenous material (e.g., yeast extract) along with the trace elements, mineral salts and/or other possibly nutritional components e.g. those derived from renewable raw materials like cornstarch, sugars and soy protein.

In some embodiments, the medium for fermentation as used herein may comprise a plant material e.g. a legume plant (e.g., soybean), a portion thereof (e.g., seeds), or an extract thereof. Exemplary legume plants include, but are not limited to, beans, peas, alfalfa, red clover, fava, vetch, and cowpeas. In particular, the legume plants can be those of relatively high protein levels in seeds, such as *Glycine*, e.g. *Glycine max*, and some other species including *Glycine soja*, *Glycine tomentella*, *Glycine tabacina* Benth, *Glycine dolichocarpa* or *Glycine clandestine*.

As used herein, legume plant materials for use in medium for fermentation can be the plant per se or a portion thereof (e.g., leave, fruit, seed, etc.), or an extract thereof. An extract can refer to a product obtained by extraction of a material, which can be carried out in a conventional manner, usually by soaking or mixing the material to be extracted in a solvent (optionally with crushing or grinding Broken) and obtaining the resultant filtrate or concentrate therefrom. Preferably, the extract as used herein refers to an aqueous extract made by extracting the material with water as a solvent. In particular embodiments, the ratio of material to be extracted to solvent may be, for example, from about 1:1 to about 1:100, from about 1:1 to about 1:50, about 1:1 to about 1:25, about 1:1 to about 1:15, about 1:1 to about 1:10, or about 1:1 to about 1:5 (w/w, g/g). The extraction can be carried out at a suitable temperature, for example, by heating, for example, 70 to 100° C. In a particular example, "extract" as used herein is an aqueous extract of the seeds of a soybean plant.

According to the present invention, the fermentation may be carried out under conditions that allow fermentation of the culture medium, for example, 20-45° C. (e.g. 20-25° C., 20-30° C., 25-30° C., 25-35° C., 30-45° C., or 30-40° C.) for a suitable period of time (e.g. 2-10 days, 2-5 days, 4-8 days, or 5-10 days). In particular, one or more steps may be performed after fermentation, e.g. sterilization, filtration, concentration, lyophilization, or any combination thereof. More particularly, sterilization is performed via, for example, heating after fermentation, and may be filtered and concentrated (e.g. dialyzed) as needed to produce a concentrated fermented composition solution. Further, the fermented composition solution may be further dried, for example, by lyophilization to obtain a fermented composition in powder form.

In some examples, the fermented composition may be prepared by a process comprising: (i) growing symbiotic microbiota e.g. yeast, lactic acid bacteria (e.g. *Lactobacillus* and/or *Lactococcus*), or a combination thereof in a medium under conditions allowing for fermentation to generate multiple metabolites; and (ii) collecting the fermented composition obtained from step (i). Optionally, the preparation process may further comprise filtering the fermented composition, sterilizing the fermented composition, and/or concentrating the fermented composition.

In some examples, the fermented composition may be prepared by a process comprising: (a) fermenting a medium comprising a carbon source, a nitrogen source and trace elements, optionally an aqueous soy bean extract with at least one lactic acid bacteria and together with at least one yeast to form a fermented liquid; (b) sterilizing said fermented liquid; (c) filtering said sterilized fermented liquid; and (d) removing water from said filtered fermented liquid to form a concentrated fermented product.

Methods for preparing fermented compositions are also described in, e.g., U.S. Pat. Nos. 6,685,973, 6,855,350, 6,733,801, US20120058104, and US20170281760, the relevant disclosures of each of which are incorporated by reference herein for the purposes or subject matter referenced herein.

In some embodiments, a subject in need of activation of TILs according to the method of the present invention includes a patient that would benefit from enhanced production of TILs.

In some embodiments, this method may include selecting a subject in need of activation of TILs and administering a fermented composition as described herein under conditions effective to activate TILs in the subject.

In some embodiments, a subject in need of activation of TILs include a candidate for adoptive T-cell therapy for treatment of a tumor or cancer. In certain examples, such candidate is determined to have a relatively low percentage/ density of TILs, as compared with a control or standard level. A control or standard level, as used herein, can refer to an average or cut off level of the percentage/density of TILs of a patient population. For example, Iseki et al. supra reviewed a population of patients with Stage II or III colorectal cancer (CRC) and set 42% as the cut-off percentage of the area occupied by TILs according to a receiver operating characteristic (ROC) analysis, dividing patients into the high-TILs group (>42%) and the low-TILs group (<42%). The percentage/density of TILs can be assayed by conventional methods in this art, for example, by immunohistochemical or HE staining and an automated imaging software program. The cut-off value may vary with patient population of different types of cancer and races.

In some embodiments, the method may include measuring TILs in a tumor sample from a patient, comparing the level of TILs in the sample with a control or standard value, and determining the patient's level of TILs. In some embodiments, based on the comparing, a patient determined to have a lower level of TILs compared with the control or standard value is selected. In some embodiments, based on the comparing, a lower level of TILs, compared to the control or standard value, further predicts the patient will have a cold tumor, a suppression tumor microenvironment and/or a poor response to anti-cancer or anti-tumor immunotherapy.

In some embodiments, the subject is afflicted with a neoplastic disease.

In some embodiments, the subject is a patient afflicted with cancer.

In some embodiments, the subject is a patient afflicted with bacteria infected cancer.

In some embodiments, the cancer to be treated include but are not limited to colon cancer, lung cancer, breast cancer, pancreatic cancer, skin cancer, brain cancer, ovarian cancer, kidney cancer, stomach cancer, head and neck cancer, esophageal cancer, bladder cancer, rectal cancer, bone cancer, uterine cancer, prostate cancer, and hematological malignancy.

In some embodiments, the subject is afflicted with a neoplastic disease having a solid tumor. Solid tumor includes, but is not limited to, sarcomas, carcinomas, lymphomas and other solid tumor cancers, including, but not limited to germ line tumors, tumors of breast cancer, bladder cancer, cervical cancer, colon cancer, the central nervous system, glioma, lung cancer, liver cancer, melanoma, mesothelioma, ovarian cancer, pancreatic cancer, stomach cancer, and thyroid cancer.

In some embodiments, the method of the present invention comprises assessing TILs prior to and/or after administration of the fermented composition. For example, TILs are assessed (for e.g., presence, number, activity) in the tumor, one or more margins of the tumor and/or tissue adjacent to the tumor.

In some embodiments, the subject as selected is one who has undergone, is undergoing or is planning to undergo an anti-cancer therapy such as that involving an immune checkpoint modular.

In some embodiments, the method of the present invention comprises administering to a subject in need an effective amount of an immune checkpoint modulator, after administration of a fermented composition as described herein wherein the TILs in the subject have been activated.

As used herein, "immune checkpoint modulator" refers to an agent that alters the activity of an immune checkpoint protein (e.g., any of those described herein) in a cell relative to a control vehicle. The term "modulator" is used herein in the broadest sense, and includes any molecule that partially or fully alters a signaling pathway regulated by one or more immune checkpoint molecules, including the signaling pathways mediated by the molecules described herein.

The immune checkpoint modulator for use herein can be an modulator (e.g., an inhibitor) of an immune checkpoint molecule, which may be PD1, CD28, CTLA-4, CD137, CD40, CD134, ICOS, KIR, LAG3, CD27, TIM-3, BTLA, GITR, TIGIT, CD96, CD226, KIR2DL, VISTA, HLLA2, TLIA, DNAM-1, CEACAM1, CD155, IDO (e.g., IDO1), TGF-beta, IL-10, IL-2, IL-15, CSF-1, IL-6, and adenosine A2A receptor (A2AR), or a ligand thereof. In some embodiments, the immune checkpoint modulator is an antibody specific to the immune checkpoint, or a ligand thereof, for example, an antibody specific to PD1 or a ligand thereof (PDL1 or PDL2). In some examples, the antibody can be a human antibody, a humanized antibody, or a chimeric antibody.

The present invention also provides a kit or combination comprising a fermented composition as described herein, optionally in combination with an immune checkpoint modulator. Such kit or combination is useful in activation of TILs and may also be effective in (i) changing tumor microenvironment to avoid suppression of anti-tumor immunity, and/or (ii) improving effects of chemotherapy and/or cancer therapy, and/or (iii) transforming cold tumor into hot tumor, and/or (iv) increasing response rate, and/or (v) reducing tumor size. Preferably, such kit or combination synergistically provides one or more effects as described herein.

In one embodiment, the medicament or therapeutic method used in combination may be used simultaneously (parallel) or sequentially. When medicaments are used in combination, the medicaments may be mixed in the same formula or put in different formulas separately, such as separate capsules, pills, tablets, and injections.

A composition can be prepared by formulating active ingredients with a physiologically or pharmaceutically acceptable carrier such that the composition is in an appropriate form for the purpose of delivery, for example. The composition of the present invention particularly comprises about 0.1% by weight to about 100% by weight of the active ingredient, wherein the percentage by weight is calculated based on the weight of the whole composition. In some embodiments, the composition of the present invention can be formulated as a pharmaceutical composition or medicament for treatment. In some embodiments, the composition of the present invention can be formulated as a food product or dietary supplement.

As used herein, "physiologically (or pharmaceutically) acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. The composition may additionally comprise lubricants; wetting agents; emulsifying and suspending agents; preservatives; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, fluid, and packaged powder.

The composition of the present invention may be delivered via any physiologically acceptable route, particularly oral. Preparation of an appropriate parenteral composition under sterile conditions may be accomplished with standard pharmacological techniques well known to persons skilled in the art.

The term "effective amount" used herein refers to the amount of an active ingredient to confer a desired biological effect in a treated subject or cell. The effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience.

The term "treating" as used herein refers to the application or administration of a composition including one or more active agents to a subject afflicted with a disorder, symptom or condition, or a progression or predisposition of the disorder, symptom or condition, with the purpose to cure, heal, alleviate, relieve, alter, remedy, ameliorate, improve, or affect the disorder, the symptom or condition, the disabilities induced by the disorder, the symptom or condition, or the progression or predisposition of the disorder, the symptom or condition.

The subject to be treated by the methods as described herein can be a mammal, particularly a human. Examples of mammals can include a rodent (e.g., mouse, rat, chipmunk, prairie dog, squirrel, beaver, gopher, hamsters, voles, gerbils, porcupines, guinea pigs, etc.), a livestock animal (e.g., pigs, cattle, goats, deer, sheep, yaks, etc.), a companion animal (e.g., cat, dog, etc.), or a primate (e.g., lemurs, monkeys, apes, humans, etc.). In particular, a subject in need of the treatment method as described herein can be a human individual that has, is suspected to have, or is at risk for having a target disease/disorder/condition, e.g. a human who is determined to have a relatively reduced level of TILs or afflicted with cancer and predicted to have poor response to cancer immunotherapy.

According to the method of the present invention, the composition can be administered to a subject in need by a proper route. In an exemplary embodiment, the composition is administered via oral route (e.g., by a solid such as a pill, tablet, or capsule, or by liquid). The composition can be delivered to one or more regions within the subject. The regions can include but are not limited to a region within the gastrointestinal tract system such as an oral cavity, stomach, small intestine, large intestine, or colon. Examples of routes of administration include but are not limited to rectal administration (e.g., by suppository, enema, upper endoscopy, upper push enteroscopy, or colonoscopy), or intubation through the nose or the mouth (e.g., by nasogastric tube, nasoenteric tube, or nasal jejunal tube).

In particular embodiments, a composition as described herein is administered via an intratumoral route. The intratumoral administration can be performed by injecting a composition as described herein into the tumor mass, immediate vicinity of the tumor, and/or the area where tumor is infiltrative growing into the healthy tissue. A single intratumoral injection into the tumor mass is usually effective when the active ingredients in the composition is delivered and the anti-tumor immune response is activated. However, multiple injections into separate regions of the tumor or different time course can also be contemplated, when necessary. In some embodiments, it is unexpectedly found that intratumoral administration of a composition as described herein provides improved therapeutic effects where the dosing amount is reduced and the dosing course is shorten, when compared with systemic administration e.g. via oral route. It is also found that intratumoral administration of a composition as described herein can effectively treat tumors in distant sites.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

Example 1: Fermentation Products by Symbiotic Microbiota

Composition X is a fermented composition generated via fermentation of symbiotic microbiota in a medium. Briefly, symbiotic microbiota including *Lactobacillus* and yeast were cultured in a medium for fermentation containing carbon source, nitrogen source and trace elements, together with an aqueous soybean extract, under conditions that allow for fermentation by the microorganisms to generate suitable metabolites. The fermentation was conducted for about 24 to 72 hours. The fermented liquid were collected, filtered to remove solid materials, and sterilized. The liquid solution thus prepared was concentrated to produce Composition X (in liquid form). Each milligram of Composition X contains the fermented broth of about 2.7 g soybean. In separate fermentation, symbiotic microbiota including *Lactobacillus*, yeast and *Lactococcus* were used to generate additional fermentation products, Compositions LT12, LT17, LT21, LT23 and LT27.

Example 2: Activation of Murine Bone Marrow Derived Dendritic Cells

At day 0, bone marrow (BM) was seeded at $2 \times 10^6$ cells per 100 mm dish in 9 ml RPMI-1640 medium containing 1% antibiotic-antimycotic, 10% FBS, 20 ng/ml rmGM-CSF. At day 3, another 9 ml RPMI-1640 medium containing 20 ng/ml rmGM-CSF were added to the plates. At day 8, BMDCs were plated in a density of $2 \times 10^5$ cells/mL resuspended in 1000 µL culture medium with 0.1 µg/mL LPS or various fermentation products (Compositions X, LT12, LT17, LT21, LT23, LT27) for 24 hours on 24-well plate in 5% $CO_2$/95% air. After the treatment, cells were collected by gentle pipetting, centrifuged at 250 g for 5 min at room temperature. The cells were adjusted to a concentration of $1.5 \times 10^5$ cells/well in PBS with 0.5% FBS. Cell suspensions were incubated with antibodies for 30 min at 4° C. FITC-conjugated CD11c antibody, PE-conjugated CD83 antibody, were obtained from BD Biosciences. Flow cytometry analysis was performed with a FACSAria Fusion. The flow cytometry data were analyzed using FlowJo v10 software.

Figure 1:
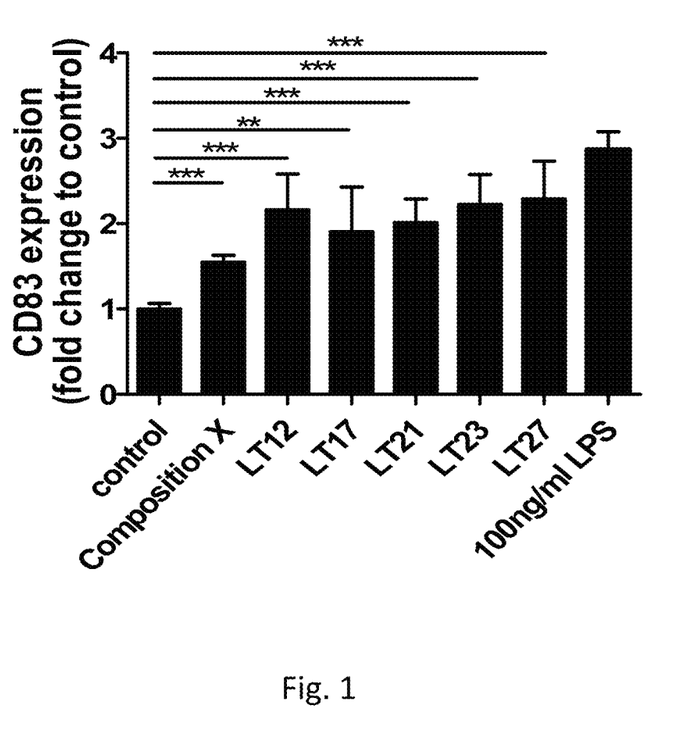
FIG. 1 shows the stimulating effects of a fermentation composition of the present invention on maturation of bone marrow dendritic cells (BMDCs). The cells were cultured and detected by anti-CD83 antibodies. *P<0.001. P<0.01. P-values were obtained by comparison by each intervention group and the control group.

As shown in FIG. 1, CD83 expression level was significantly increased as a result of treatment with various fermentation products of the present invention as compared with the control. It indicates that the fermented composition of the present invention is effective in stimulating BMDC maturation.

Example 3: Colon Cancer Mouse Model and Animal Tests

BALB/c mice were implanted subcutaneous (s.c.) with CT-26 $2 \times 10^5$ cells on Day 0. Mice were randomized into treated or untreated groups (n=3 for each group) when the tumors volume reached 50 mm³ approximately on Day 4.

3.1 Treatment with Composition X

Mice were treated with 15% Composition X (10 mL/kg) by oral gavage daily from Day 4 to Day 11 for group 2/3. Mice were treated with ddH₂O (10 mL/kg) by oral gavage daily from Day 4 to Day 11 for group 1. Mice were treated with anti-PD1 antibody at dose of 10 mg/kg by i.p. injection on Day 4, 6, 8 and 10 for group 3. Tumors volume was measured twice weekly. The survival rates were also determined. Mice were sacrificed on Day 11 for group 1/2/3 and tumors were collected.

3.2 Treatment with Composition LT12

Figure 2:
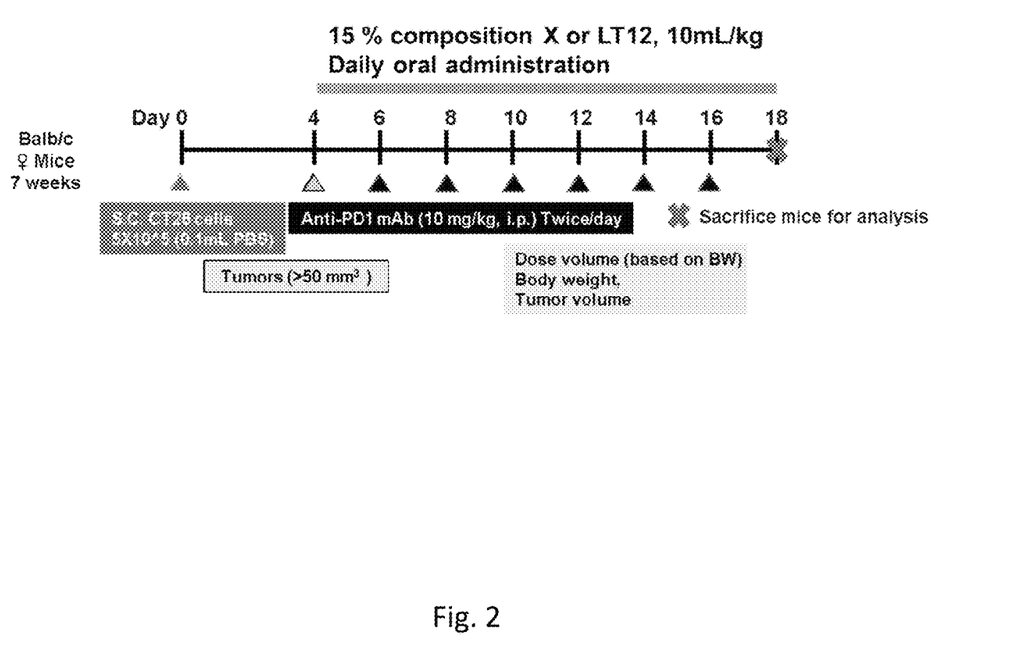
FIG. 2 is a schematic illustration of an experimental design for studying the effect of a fermentation composition of the present invention via oral administration in a colon cancer mouse model. The mice were transplanted with colon cancer CT26 cells and treated with the fermented composition, optionally in combination with an anti-PD1 antibody.

Mice were treated with 15% Composition LT12 (10 mL/kg) by oral gavage daily until day 17. Mice were treated with ddH$_{2O}$ (Sterilized, 10 mL/kg) by oral gavage daily until day 17. Mice were treated with anti-PD1 antibody at dose of 10 mg/kg by i.p. injection on day 6, 8, 10, 12, 14 and 16. Tumor Volume of each side was measured on day 4, 6, 8, 11, 13, 15 and 18. Mice were sacrificed on Day 18 and tumors were collected. FIG. 2 shows the schedule of treatment.

3.3 Immunohistochemistry of Tumors

The tumors were fixed in liquid nitrogen embedded in OCT compound, and kept at −80° C. Section the block at a range of 5 μm and place on slides. The sections were incubated with ice-cold blocking solution (PBS containing 5% Goat serum) for 30 min and the primary antibody (Anti-CD4 antibody, Anti-CD8 antibody and Anti-CD86 antibody) overnight at 4° C., followed by three washes with PBS, and finally incubated with secondary antibody Goat Anti-Rabbit IgG H&L and Goat Anti-Rat IgG H&L for 1 h. Nucleus was stained with EverBrite mounting medium with DAPI (Biotium).

Figure 3:
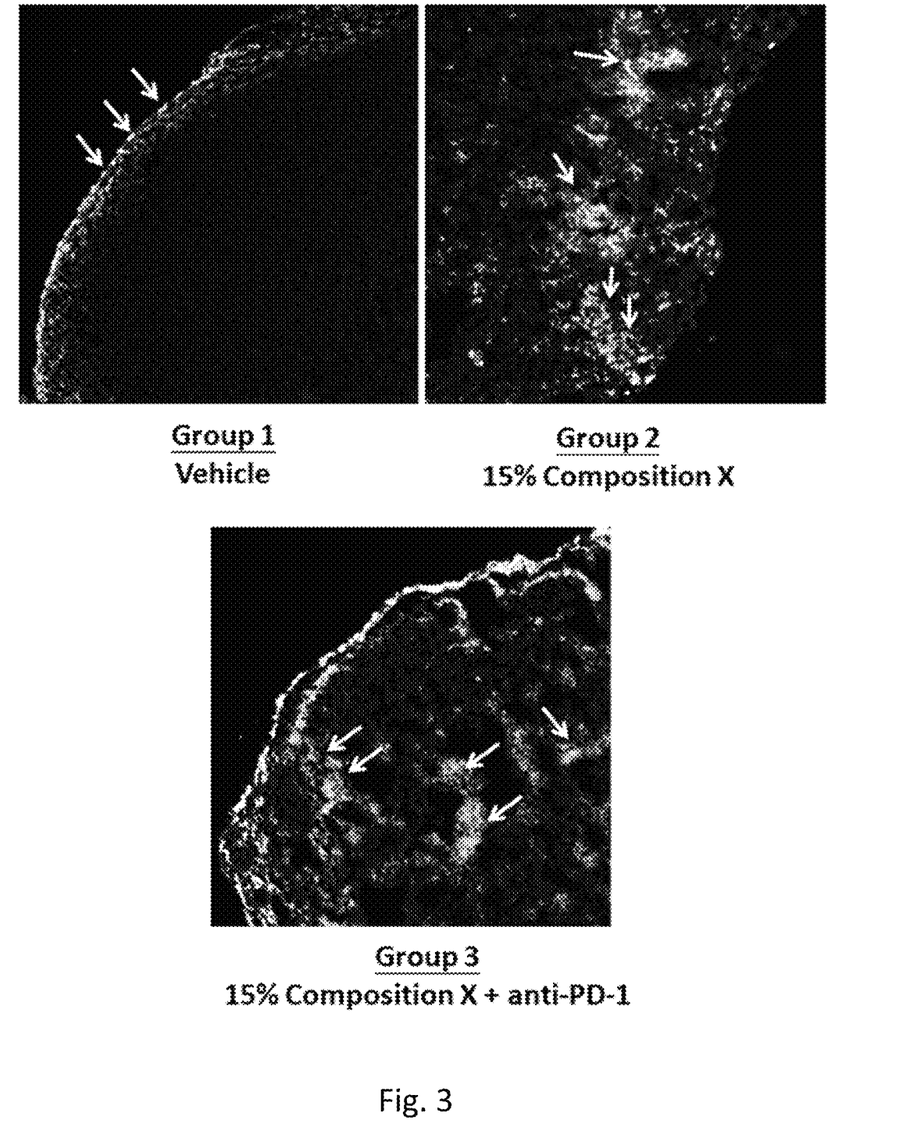
FIG. 3 is an image showing the results of immunohistochemistry analysis of tumors from the colon cancer mouse model, including the immunofluorescent staining of CD4 T cells, CD8 T cells or CD86 dendritic cells. The mice were transplanted with colon cancer CT26 cells and treated with a vehicle control, Composition X, or combinations of Composition X with an anti-PD1 antibody.

As shown in FIG. 3, in group 1 (the vehicle group), the tumor infiltrating CD4⁺/CD8⁺ T cells/CD86+dendritic cells were present but inactivated (gathering outside the tumor, failing to migrate into the tumor), while in group 2 (composition X group) and group 3 (a combination of composition X and anti-PD1 antibody), the tumor infiltrating CD4⁺/CD8⁺ T cells/CD86+dendritic cells migrating into the tumors were significantly observed.

Figure 4:
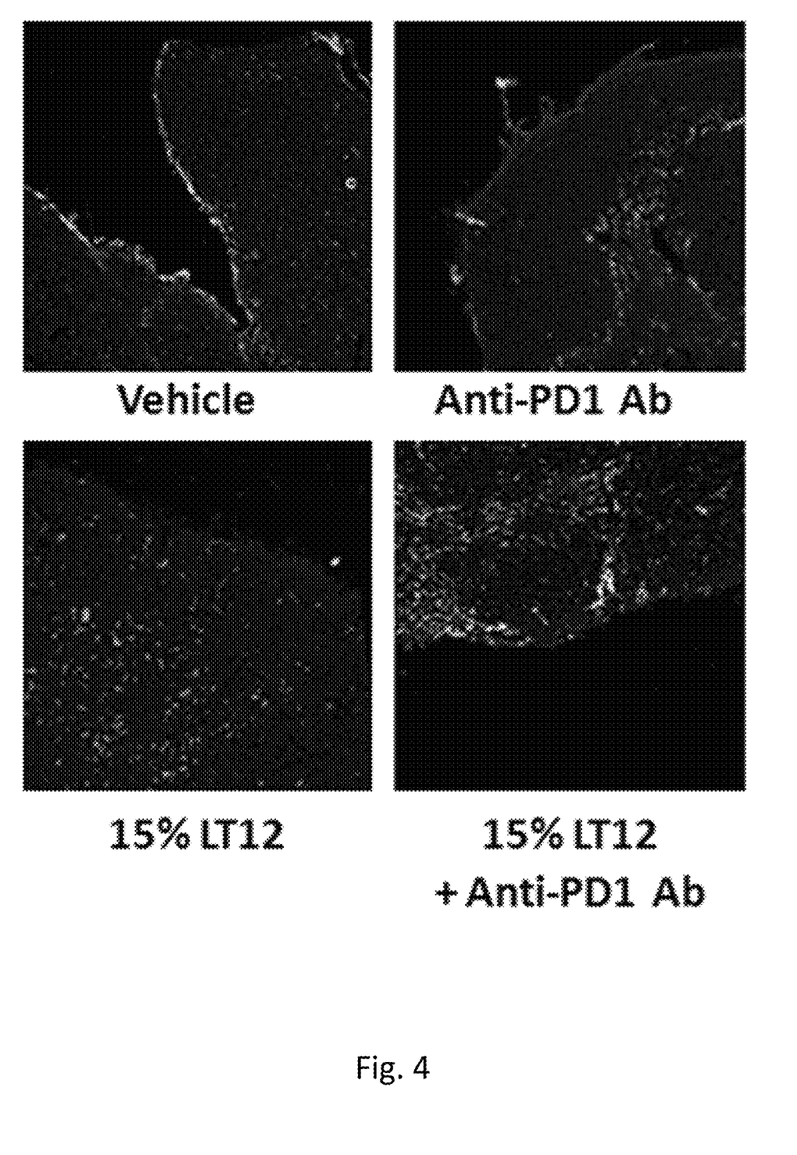
FIG. 4 is an image showing the results of immunohistochemistry analysis of tumors from the colon cancer mouse model, including the immunofluorescent staining of CD4 T cells, CD8 T cells or CD86 dendritic cells. The mice were transplanted with colon cancer CT26 cells and treated with a vehicle control, an anti-PD1 antibody, Composition LT12, or a combination of Composition LT12 with an anti-PD1 antibody. The tumor samples were obtained from the mice and subjected to the immunohistochemistry analysis.

Similarly, as shown in FIG. 4, in the vehicle group, the tumor infiltrating CD4⁺/CD8⁺ T cellswere present but inactivated (gathering outside the tumor, but not migrating into the tumor); while in the group of composition LT12 alone or anti-PD1 antibody alone, the tumor infiltrating CD4⁺/CD8⁺ T cells migrating into the tumors were increased, and particularly in the group of a combination of composition LT12 and anti-PD1 antibody, the tumor infiltrating CD4⁺/CD8⁺ T cells migrating into the tumors were significantly observed.

3.3 Tumor CD8 T Cell Analysis

Tumors were extracted and finely minced. Tumor tissue was additionally blended with the gentleMACS Dissociator (Miltenyi cat. 130-096-427) and digested with MACS Miltenyi Tumour Dissociation Kit for mouse (Miltenyi Biotec cat. 130-096-730) according to manufacturer's instructions. Dissociated tumor cells were washed with RPMI Medium 1640 (Gibco cat. 11875-093) and lysed with RBC Lysis Solution (Sigma cat. R7757). The cells were adjusted to a concentration of 4×10⁶ cells/well in PBS with 0.5% FBS. Cell suspensions were incubated with antibodies for 30 min at 4° C. PE-conjugated CD8α antibody (#553033 was obtained from BD Biosciences). Flow cytometry analysis was performed with a FACSAria Fusion (BD Biosciences). The flow cytometry data were analyzed using FlowJo v10 software (Tree Star, San Carlos, Calif.).

Figure 5:
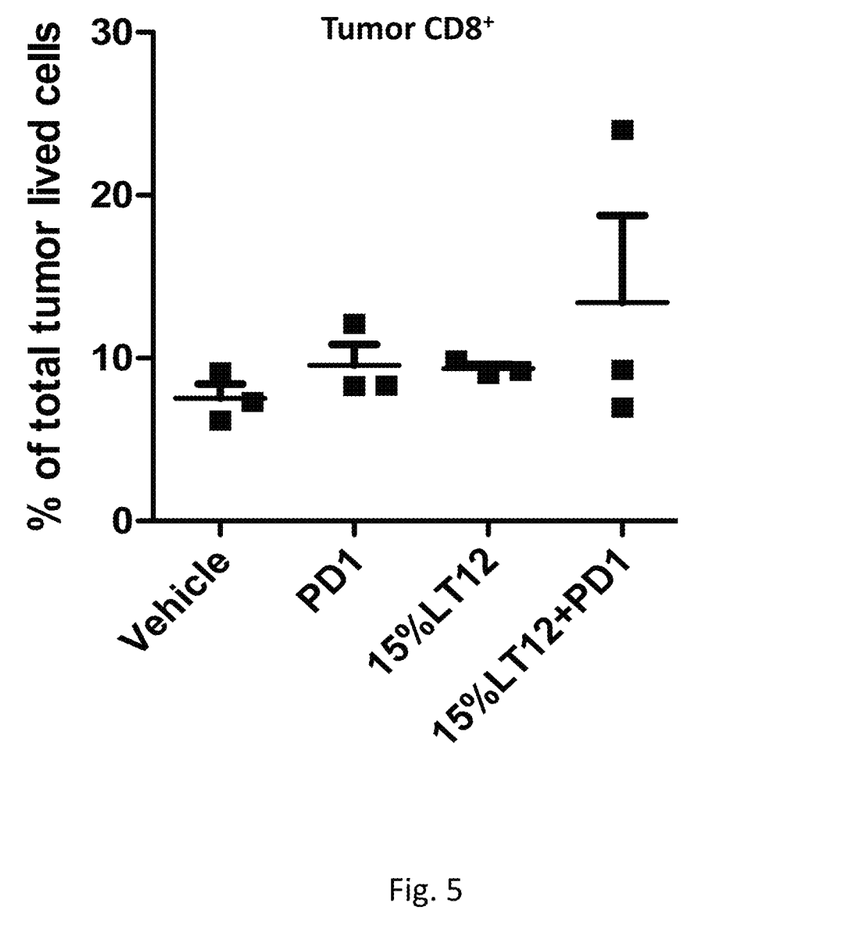
FIG. 5 is a chart showing the results of tumor CD8 T cell analysis in the colon cancer mouse model. The mice were transplanted with colon cancer CT26 cells and treated with a vehicle control, an anti-PD1 antibody, Composition LT12, or a combination of Composition LT12 with an anti-PD1 antibody. The tumor samples obtained from the mice were digested to provide cell suspensions including dissociated tumor cells which were quantified to determine the amount of CD8 T cell in the total tumor lived cells.

As shown in FIG. 5, in the vehicle group, the number of the CD8⁺ T cells associated with the tumor were lower, while in the group of composition LT12 alone and anti-PD1 antibody alone, the number of the CD8⁺ T cells associated with the tumor were higher, and particularly in the group of a combination of composition LT12 and anti-PD1 antibody, the number of the CD8⁺ T cells associated with the tumor was expressly higher.

The results indicate that the fermented composition of the present invention is effective in activating TILs, promoting the migration of TILs into the tumor and increasing the amount of intratumor CD8⁺ T cells.

3.4 Tumor Size and Survival Rate

Figure 6:
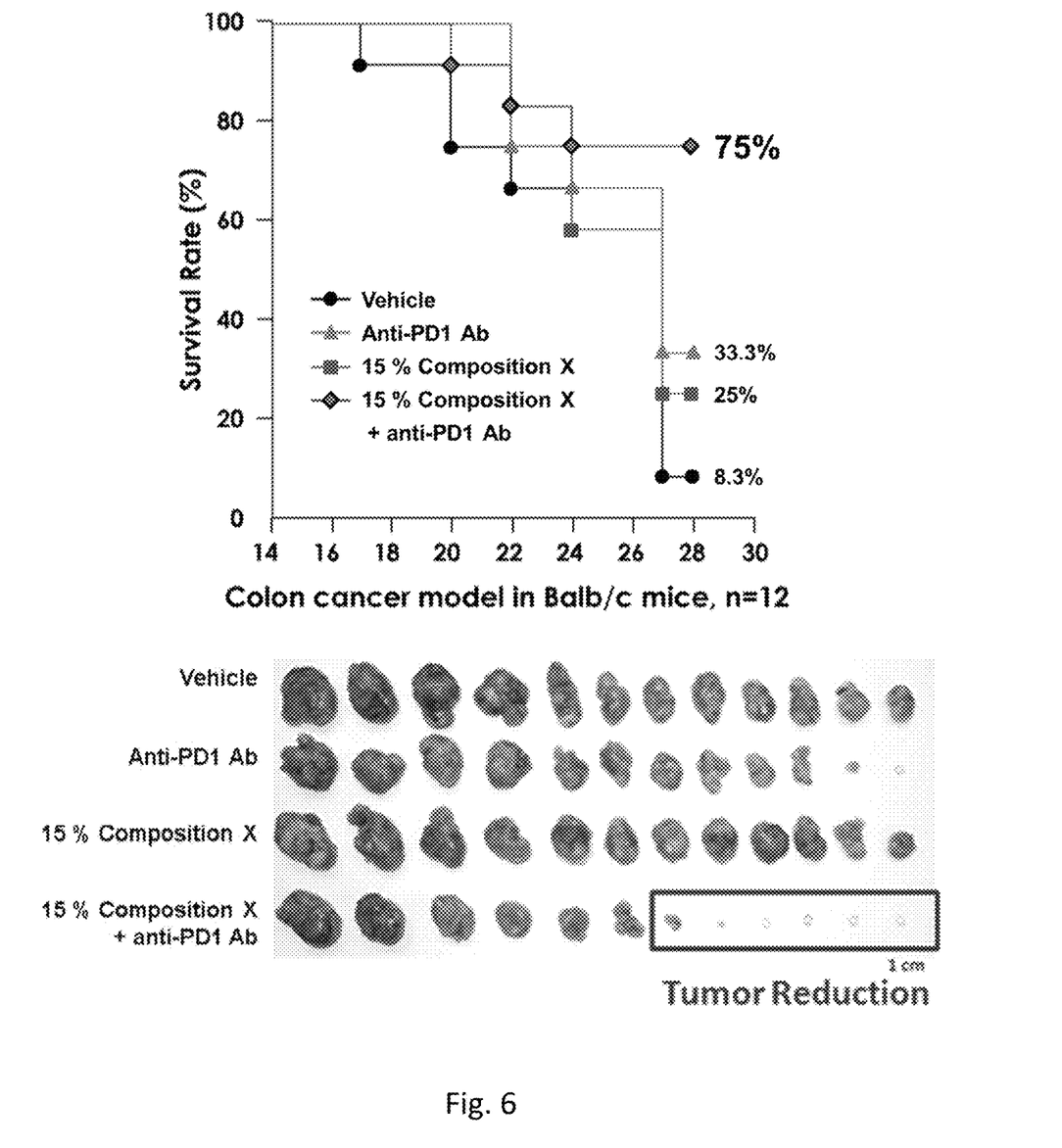
FIG. 6 includes charts showing survival rate and tumor size of the colon cancer mouse model. The mice were transplanted with colon cancer CT26 cells and treated with a vehicle control, an anti-PD1 antibody, Composition X, or a combination of Composition X with an anti-PD1 antibody.
Figure 7:
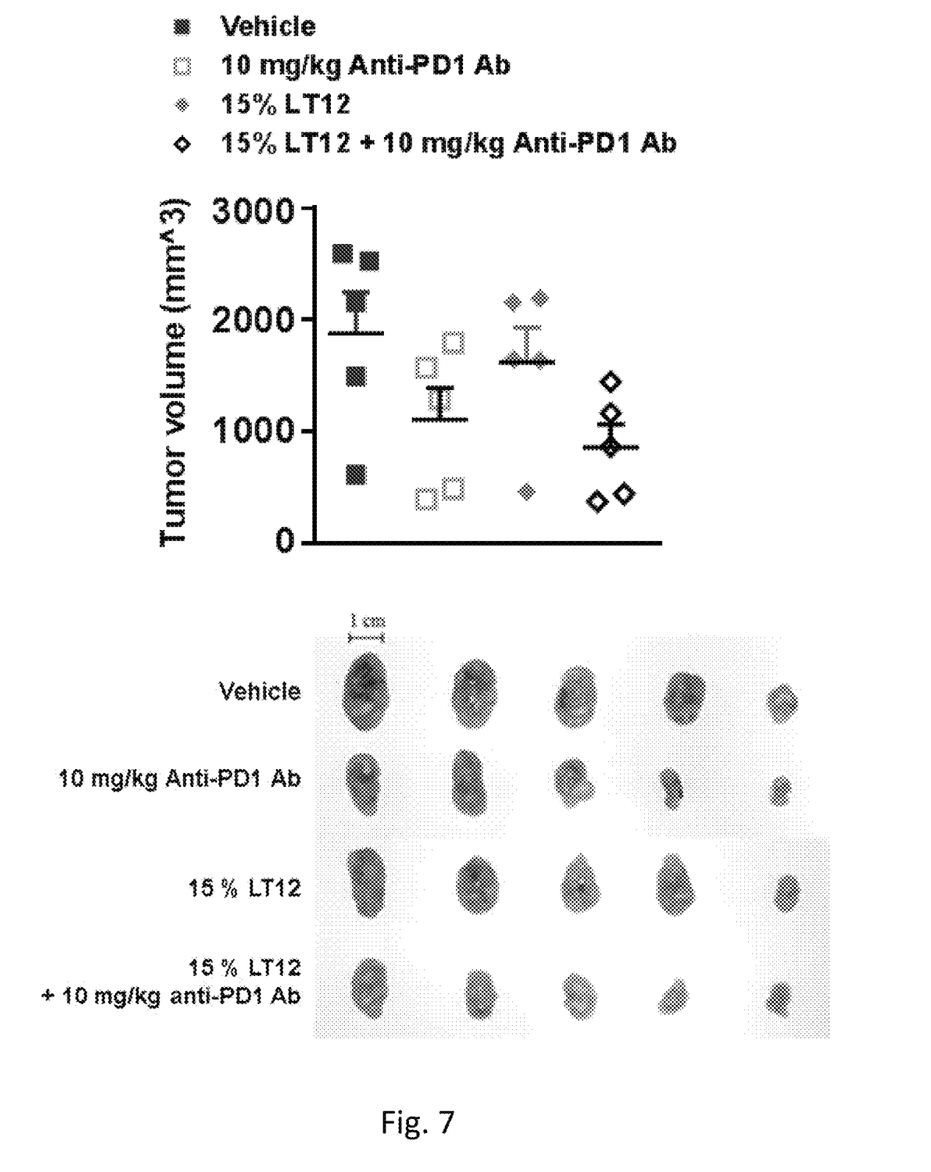
FIG. 7 includes charts showing survival rate and tumor size of the colon cancer mouse model. The mice were transplanted with colon cancer CT26 cells and treated with a vehicle control, an anti-PD1 antibody, Composition LT12, or a combination of Composition LT12 with an anti-PD1 antibody.

As shown in FIG. 6, composition X alone or an anti-PD1 antibody alone improves animal survival rate (25% or 33.3%) as compared with vehicle (8%); a combination of composition X and an anti-PD1 antibody significantly improves animal survival rate (75%) and reduces tumor size, as compared with vehicle, composition X alone or an anti-PD1 antibody alone. Similarly, FIG. 7 shows the effects of cancer therapy using the fermented composition of the present invention that the tumor size was reduced as a result of treatment of composition LT12 alone or an anti-PD1 antibody alone, and particularly the tumor size was significantly reduced as a result of combined treatment of composition LT12 and an anti-PD1 antibody.

Example 4: Intratumoral Administration of Composition X

BALB/c mice were implanted subcutaneous (s.c.) with CT-26 2×10⁵ cells on Day 0 on the right flank and the left flank, respectively. Mice were randomized into treated or untreated groups (n=3 for each group) when the tumors volume reached 50 mm³ approximately on Day 5. Mice were treated with 10% Composition X (10 ml/kg) via intratumoral injection on Day 5, 7 and 9 (three doses). Mice were treated with ddH₂O (Sterilized, 10 mL/kg) via intratumoral injection as a blank control. Mice were treated with 4 μg anti-OX40 antibody via intratumoral injection on Day 6, 8 and 10. Tumor Volume of each side was measured on day 5, 8, 11, 13, 15, 18 and 20. Mice were sacrificed on Day 25.

Figure 8:
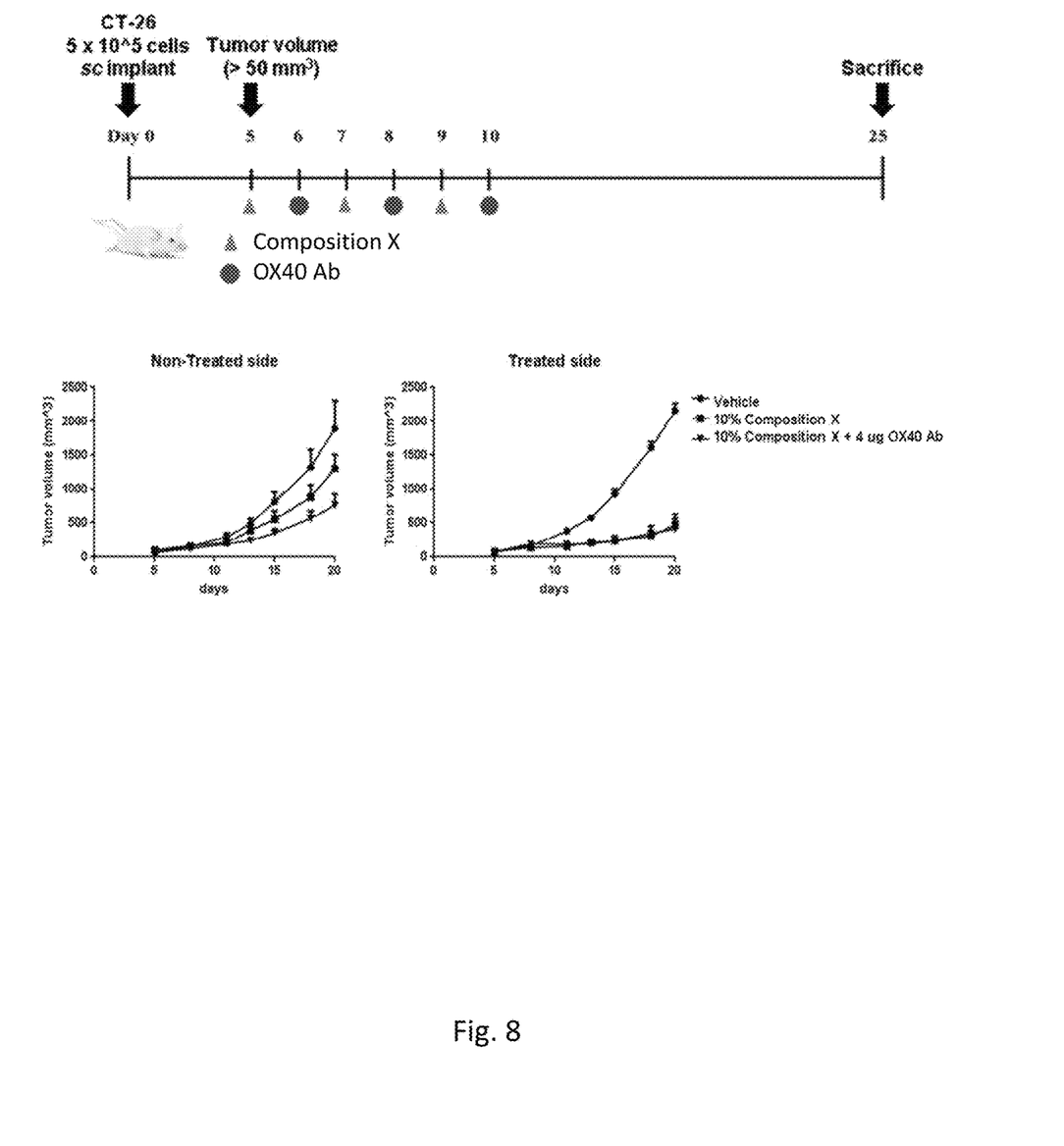
FIG. 8 includes a schematic illustration of an experimental design for studying the effect of a fermentation composition of the present invention via intratumoral administration in a colon cancer mouse model, and charts showing the tumor size of the colon cancer mouse model. The mice were transplanted with colon cancer CT26 cells and treated with a vehicle control, Composition X, or a combination of Composition X with an anti-PD1 antibody.

As shown in FIG. 8, in the treated side, the tumor volume was significantly reduced as a result of intratumoral administration of 10% Composition X alone (at a lower dose via only three injections, compared with 15% Composition X at a higher dose via daily oral administration as in Example 3) or in combination with anti-OX40 antibody, as compared with the vehicle group; and surprisingly, the therapeutic effect was also observed in the untreated side. The results show that intratumoral administration of the fermented composition of the present invention, optionally in combination with an immune checkpoint modulator, provides advantageous therapeutic effects including a lower dose for each injection, a reduced number of dosing, and successful tumor responses in distant (untreated) sites.

In this study, it is found that a fermentation product by symbiotic microbiota as described herein is effective in activating tumor infiltrating cells in tumor animal models, thus providing superior therapeutic effects in reducing tumor size and improving survival rate, especially in combination with an immune checkpoint modulator. It is also found that intratumoral administration of a fermentation product by symbiotic microbiota as described herein provides superior therapeutic effects where the dosing amount is reduced, the dosing course is shorten, and even tumors in distant sites thought to be unresponsive can now be successfully treated.

What is claimed is:

1. A method for activating tumor-infiltrating lymphocytes (TILs) in a subject in need thereof, comprising administering to the subject a fermentation composition which is generated via fermentation of symbiotic microbiota in a medium comprising an aqueous soybean extract, wherein the symbiotic microbiota comprises (i) at least two or more lactic acid bacteria strains, or (ii) at least two or more yeast strains, or (iii) at least one or more lactic acid bacteria strains and at least one or more yeast strains, in an amount effective in increasing production or activity of TILs in the subject, wherein the subject has been determined to have a lower level of TILs as compared to a reference level prior to the administration of the fermentation composition.

2. The method of claim 1, wherein the medium comprises carbon source, nitrogen source and trace elements.

3. The method of claim 1, wherein the fermented composition comprises multiple metabolites that are generated via the fermentation.

4. The method of claim 1, wherein the fermented composition is prepared by a process comprising
   i) growing the symbiotic microbiota in the medium under conditions allowing for fermentation to generate multiple metabolites; and
   ii) collecting the fermented composition obtained from step (i).

5. The method of claim 4, wherein the preparation process further comprises sterilizing, filtering and/or concentrating the fermented composition obtained from step (ii).

6. The method of claim 1, wherein the amount of the fermented composition is effective in (i) changing tumor microenvironment to avoid suppression of anti-tumor immunity, and/or (ii) improving effects of chemotherapy and/or cancer therapy, and/or (iii) transforming cold tumor into hot tumor, and/or (iv) increasing response rate, and/or (v) reducing tumor size, and/or (vi) improving survival rates, in the subject.

7. The method of claim 1, wherein the subject is afflicted with a neoplastic disease.

8. The method of claim 1, wherein the subject is afflicted with cancer.

9. The method of claim 8, wherein the cancer selected from the group consisting of colon cancer, lung cancer, breast cancer, pancreatic cancer, skin cancer, brain cancer, ovarian cancer, kidney cancer, stomach cancer, head and neck cancer, esophageal cancer, bladder cancer, rectal cancer, bone cancer, uterine cancer, prostate cancer, and hematological malignancy.

10. The method of claim 1, wherein the subject is afflicted with bacteria infected tumor.

11. The method of claim 1, wherein the subject has undergone, is undergoing or is planning to undergo an immune therapy against a neoplastic disease.

12. The method of claim 1, wherein the TILs include CD4+, CD8+ and/or CD86+dendritic cells.

13. The method of claim 1, wherein the TILs include intratumor TILs, stromal TILs or both.

14. The method of claim 1, wherein the composition is administered via oral administration or injection administration.

15. The method of claim 1, wherein the composition is administered via intratumoral administration.

16. The method of claim 1, wherein the method further comprising, prior to administration of the fermentation composition, measuring TILs in a tumor sample from the subject, comparing the level of TILs in the sample with a control value, and determining the subject's level of TILs, wherein based on the comparing, a patient having a lower level of TILs is selected.

17. The method of claim 16, wherein the patient has a cold tumor, a suppression tumor microenvironment and/or a poor response to anti-cancer or anti-tumor immunotherapy.

18. The method of claim 1, wherein the reference level represents an average level of TIL in a patient population prior to or without treatment by the fermentation composition.

* * * * *